United States Patent [19]
Barnes et al.

[11] Patent Number: 5,849,958
[45] Date of Patent: Dec. 15, 1998

[54] 1,4,DIARYL-2-FLUORO-2-BUTENE INSECTICIDAL AND ACARICIDAL AGENTS

[75] Inventors: Keith D. Barnes, Newtown, Pa.; Yulin Hu, Plainsboro, N.J.

[73] Assignee: American Cyanamid Company, Madison, N.J.

[21] Appl. No.: 819,623

[22] Filed: Mar. 17, 1997

[51] Int. Cl.$^6$ ..................................................... C07C 41/22
[52] U.S. Cl. ................ 568/634; 568/637; 568/812; 558/384; 514/479
[58] Field of Search ...................... 568/634, 678, 568/812, 813, 329; 558/384, 410; 514/479

[56] References Cited

U.S. PATENT DOCUMENTS 5,248,834   9/1993   Elliott et al. ................ 52/638

FOREIGN PATENT DOCUMENTS 2288803   1/1995   United Kingdom .
WO 94/06741   3/1994   WIPO ........................... C07C 43/29

Primary Examiner—Gary Geist
Assistant Examiner—Sreeni Padmanabhan
Attorney, Agent, or Firm—Joseph M. Mazzarese

[57] ABSTRACT

Pesticidal 1,4-diaryl-2-fluoro-2-butene compounds having the structural formula I

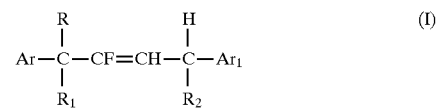

and compositions and methods comprising those compounds for the control of insect and acarid pests.

6 Claims, No Drawings

1,4,DIARYL-2-FLUORO-2-BUTENE INSECTICIDAL AND ACARICIDAL AGENTS

BACKGROUND OF THE INVENTION

Insect and acarid pests destroy growing and harvested crops. In the United States, agronomic crops must compete with thousands of those pests. In particular, tobacco budworms and southern armyworms are especially devastating to crops.

Tobacco budworms cause tremendous economic losses in agronomic crops. In particular, budworms devastate cotton crops by feeding on green bolls. Control of budworms is complicated by their resistance to many common insecticides, including organophosphates, carbamates and pyrethroids.

In spite of the commercial insecticides and acaricides available today, damage to crops, both growing and harvested, caused by insect and acarid pests still occurs. Accordingly, there is ongoing research to create new and more effective insecticidal and acaricidal agents.

Certain fluoroolefin compounds are known to possess insecticidal and acaricidal activity (see, e.g., U.S. Pat. No. 5,248,834; GB 2,288,803-A and WO 94/06741). The fluoroolefin compounds disclosed in GB 2,288,803-A and WO 94/06741 are outside the scope of the present invention. U.S. Pat. No. 5,248,834 generically discloses certain 1-aryl-1-(3-aryl-1-fluoroprop-1-enyl)cyclopropane compounds. However, that patent does not provide a method to prepare those compounds. In fact, U.S. Pat. No. 5,248,834 does not provide a method to prepare any fluoroolefin compounds.

It is, therefore, an object of the present invention to provide compounds which are highly effective for the control of insect and acarid pests.

It is also an object of the present invention to provide a method for the control of insect and acarid pests.

It is a further object of this invention to provide a method for the protection of growing and harvested crops from damage caused by insect and acarid attack and infestation.

These and other objects of the present invention will become more apparent from the detailed description thereof set forth below.

SUMMARY OF THE INVENTION

The present invention comprises 1,4-diaryl-2-fluoro-2-butene compounds which are useful as insecticidal and acaricidal agents. Those compounds are also useful for protecting plants from damage caused by insect and acarid attack and infestation.

The 1,4-diaryl-2-fluoro-2-butene compounds of the present invention have the structural formula I

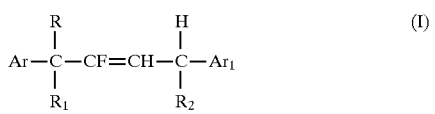

wherein
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups,
  1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
  a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;
R and $R_1$ are each independently hydrogen, $C_1$–$C_4$alkyl, $C_1$–$C_4$haloalkyl, $C_3$–$C_6$cycloalkyl or $C_3$–$C_6$halocycloalkyl, or R and $R_1$ taken together with the carbon atom to which they are attached form a $C_3$–$C_6$cycloalkyl ring optionally substituted with any combination of from one to three halogen or $C_1$–$C_4$alkyl groups;
$R_2$ is hydrogen, Cl, Br, cyano or $OR_3$;
$R_3$ is hydrogen or $C_1$–$C_4$alkyl; and
$Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups,
  phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
  1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
  a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, and
  the optical isomers thereof, and
  the cis and trans isomers thereof.

This invention also comprises compositions containing those compounds and methods for using those compounds and compositions Advantageously, it has been found that the 1,4-diaryl-2-fluoro-2-butene compounds of the present invention, and compositions containing them, are useful for the control of insect and acarid pests. The compounds of this invention are also useful for the protection of plants from damage caused by insect and acarid attack and infestation.

DETAILED DESCRIPTION OF THE INVENTION

The present invention provides a method for the control of insect or acarid pests which comprises contacting said pests or their food supply, habitat or breeding grounds with a pesticidally effective amount of a 1,4-diaryl-2-fluoro-2-butene compound of formula I.

The present invention also provides a method for the protection of growing plants from attack or infestation by insect or acarid pests which comprises applying to the foliage of the plants, or to the soil or water in which they are growing, a pesticidally effective amount of a 1,4-diaryl-2-fluoro-2-butene compound of formula I.

The 1,4-diaryl-2-fluoro-2-butene compounds of the present invention have the structural formula I

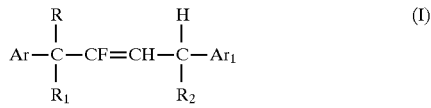

wherein Ar, Ar$_1$, R, R$_1$ and R$_2$ are as described hereinabove for formula I.

In formula I above, 5- and 6-membered heteroaromatic rings include, but are not limited to, pyridyl, pyrazolyl, imidazolyl, triazolyl, isoxazolyl, tetrazolyl, pyrazinyl, pyridazinyl, triazinyl, furanyl, thienyl and thiazolyl rings each optionally substituted as described in formula I above.

Exemplary of halogen hereinabove are fluorine, chlorine, bromine and iodine. The terms "$C_1$–$C_4$haloalkyl", "$C_3$–$C_6$halocycloalkyl" and "$C_1$–$C_4$haloalkoxy" are defined as a $C_1$–$C_4$alkyl group, a $C_3$–$C_6$cycloalkyl group and a $C_1$–$C_4$alkoxy group substituted with one or more halogen atoms, respectively.

Preferred formula I 1,4-diaryl-2-fluoro-2-butene compounds of the present invention are those wherein Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R and R$_1$ are each independently hydrogen, $C_1$–$C_4$alkyl, $C_1$–$C_4$haloalkyl, $C_3$–$C_6$cycloalkyl or $C_3$–$C_6$halocycloalkyl provided that at least one of R and R$_1$ is other than hydrogen, or R and R$_1$ taken together with the carbon atom to which they are attached form a $C_3$–$C_6$cycloalkyl ring optionally substituted with any combination of from one to three halogen or $C_1$–$C_4$alkyl groups;

R$_2$ is hydrogen, Cl, Br, cyano or OR$_3$;

R$_3$ is hydrogen or $C_1$–$C_4$alkyl; and

Ar$_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups, 3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or 3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

More preferred insecticidal and acaricidal agents of the present invention are those wherein Ar is phenyl optionally substituted with any combination of from one 3to three halogen, $C_1$–$C_4$alkyl, $C_1$–$C_4$haloalkyl, $C_1$–$C_4$alkoxy or $C_1$–$C_4$haloalkoxy groups;

R is isopropyl or cyclopropyl and R$_1$ is hydrogen, or R and R$_1$ are methyl, or R and R$_1$ taken together with the carbon atom to which they are attached form a cyclopropyl ring;

R$_2$ is hydrogen; and

Ar$_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

Most preferred 1,4-diaryl-2-fluoro-2-butene compounds of this invention are those wherein Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R is cyclopropyl and R$_1$ is hydrogen;

R$_2$ is hydrogen; and

Ar$_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

Formula I compounds of this invention which are particularly effective insecticidal agents include 1-[1-(p-chlorophenyl)-2-fluoro-4-(4-fluoro-3-phenoxyphenyl)-2-butenyl]cyclopropane, (R,S)-(Z)-;

1-[1-(p-chlorophenyl)-2-fluoro-4-(m-phenoxyphenyl)-2-butenyl]cyclopropane, (R,S)-(Z)-;

4-(p-chlorophenyl)-3-fluoro-1-(4-fluoro-3-phenoxyphenyl)-5-methyl-2-hexene, (R,S)-(Z)-;

4-(p-chlorophenyl)-3-fluoro-5-methyl-1-(m-phenoxyphenyl)-2-hexene, (R,S)-(Z)-;

4-(p-ethoxyphenyl)-3-fluoro-1-(4-fluoro-3-phenoxyphenyl)-5-methyl-2-hexene, (R,S)-(Z)-;

1-[1-(p-ethoxyphenyl)-2-fluoro-4-(4-fluoro-3-phenoxyphenyl)-2-butenyl]cyclopropane, (R,S)-(Z)-;

4-(p-ethoxyphenyl)-3-fluoro-5-methyl-1-(m-phenoxyphenyl)-2-hexene, (R,S)-(Z)-;

4-(p-ethoxyphenyl)-3-fluoro-1-[m-(p-fluorophenoxy)-phenyl]-5-methyl-2-hexene, (R,S)-(Z)-;

1-{1-(p-chlorophenyl)-2-fluoro-4-[m-(p-fluorophenoxy)-phenyl]-2-butenyl}cyclopropane, (R,S)-(Z)-;

1-[2-fluoro-4-(4-fluoro-3-phenoxyphenyl)-1-(p-fluorophenyl)-2-butenyl]cyclopropane, (R,S)-(Z)-;

1-[1-(p-ethoxyphenyl)-2-fluoro-4-(m-phenoxyphenyl)-2-butenyl]cyclopropane, (R,S)-(Z)-;

1-[2-fluoro-1-(p-fluorophenyl)-4-(m-phenoxyphenyl)-2-butenyl]cyclopropane, (R,S)-(Z)-;

4-(p-chlorophenyl)-3-fluoro-4-methyl-1-(m-phenoxyphenyl)-2-pentene, (Z)-;

4-(p-chlorophenyl)-3-fluoro-1-(4-fluoro-3-phenoxyphenyl)-4-methyl-2-pentene, (Z)-;

1-(p-chlorophenyl)-1-[1-fluoro-3-(m-phenoxyphenyl)propenyl]cyclopropane, (Z)-; and 1-(p-chlorophenyl)-1-[1-fluoro-3-(4-fluoro-3-phenoxyphenyl)propenyl]cyclopropane, (Z)-, among others.

Flow Diagram I illustrates a method for preparing 1,4-Diaryl-2-fluoro-2-butene compounds of the present invention wherein R and R$_1$ are each independently $C_1$–$C_4$alkyl, $C_1$–$C_4$haloalkyl, $C_3$–$C_6$cycloalkyl or $C_3$–$C_6$halocycloalkyl, or R and R$_1$ taken together with the carbon atom to which they are attached form a $C_3$–$C_6$cycloalkyl ring optionally substituted with any combination of from one to three halogen or $C_1$–$C_4$alkyl groups; R$_2$ is hydrogen; and the double bond is in the (Z)- configuration. This method comprises: reacting an arylacetonitrile of formula II with a selective reducing agent, such as diisobutyl-aluminum hydride, and quenching with water to form a 2-arylacetaldehyde of formula III; reacting the formula III compound with a zinc/triphenyl phosphine/carbon tetrabromide mixture to form a 3-aryl-1,1-dibromo-1-propene of formula IV; reacting the formula IV compound with a base such as an alkyllithium and phenyl cyanate to form a 4-aryl-2-butynenitrile of formula V; reacting the formula V compound with cesium fluoride, potassium hydrogen fluoride and water in N,N-dimethylformamide to form a 4-aryl- 3-fluoro-2-butenenitrile, (Z)- of formula VI; selectively reducing the formula VI compound with a reducing agent such as diisobutylaluminum hydride and quenching with water to form a 4-aryl-3-fluoro-2-butenal, (Z)- of formula VII; reducing the formula VII compound with a conventional reducing agent such as lithium aluminum hydride or sodium borohydride to form a 4-aryl-3-fluoro-2-buten-1-ol, (Z)- of formula VIII; reacting the formula VIII compound with a brominating agent, such as a triphenyl phosphine and bromine mixture, in the presence of a solvent, such as a halogenated hydrocarbon, to form a 4-aryl-1-bromo-3-fluoro-2-butene, (Z)- of formula IX; and reacting the formula IX compound with about 0.0025 to 0.1 molar equivalent of a palladium catalyst, such as bis (dibenzylideneacetone)palladium(0) (Pd(dba)$_2$), bis(acetonitrile)palladium(II) chloride, bis(triphenylphosphine)palladium(II) chloride, tetrakis (triphenylphosphine) palladium(0) and the like, at least about 2 molar equivalents of a base, such as an alkali metal carbonate, an alkaline earth metal carbonate, an alkali metal hydrogen carbonate, an alkali metal hydroxide, an alkaline earth metal hydroxide, an alkali metal $C_1$–$C_6$ alkoxide and the like, and a boronic acid of formula X in the presence of a solvent, such as an aromatic hydrocarbon, a halogenated aromatic hydrocarbon, a $C_1$–$C_4$ alcohol, and the like, and mixtures thereof.

FLOW DIAGRAM I

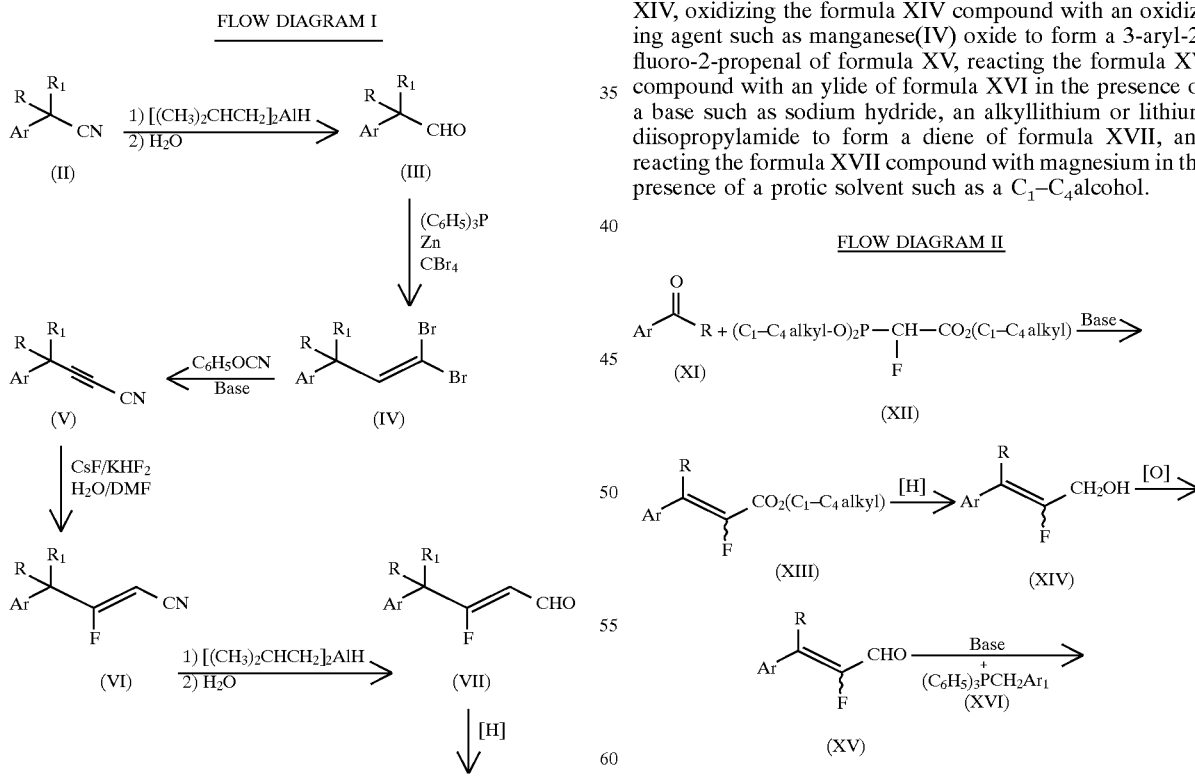

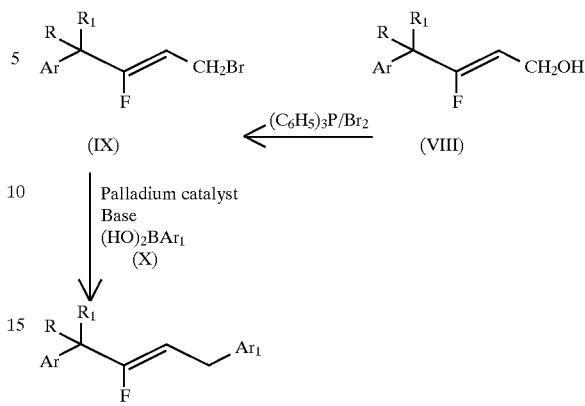

Formula I compounds wherein the double bond is in the (E)- configuration may be prepared by isomerizing certain intermediate compounds described hereinabove which are predominantly in the (Z)- configuration using conventional procedures such as exposure to light.

Formula I compounds wherein $R_1$ and $R_2$ are hydrogen may be prepared, as indicated in Flow Diagram II, by reacting a ketone or aldehyde of formula XI with an ester of formula XII in the presence of a base such as sodium hydride or lithium diisopropylamide to form a 3-aryl-2-fluoro-2-propenate of formula XIII, reducing the formula XIII compound with a reducing agent such as lithium aluminum hydride to form a 3-aryl-2-fluoro-2-propen-1-ol of formula XIV, oxidizing the formula XIV compound with an oxidizing agent such as manganese(IV) oxide to form a 3-aryl-2-fluoro-2-propenal of formula XV, reacting the formula XV compound with an ylide of formula XVI in the presence of a base such as sodium hydride, an alkyllithium or lithium diisopropylamide to form a diene of formula XVII, and reacting the formula XVII compound with magnesium in the presence of a protic solvent such as a $C_1$–$C_4$ alcohol.

FLOW DIAGRAM II

FLOW DIAGRAM II -continued

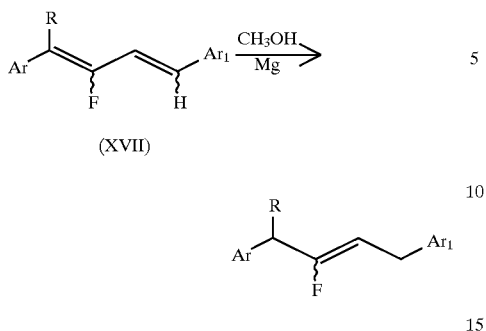

Alternatively, formula XVII diene compounds may be prepared, as indicated in Flow Diagram III, by reacting a 3-aryl-2-fluoro-2-propen-1-ol of formula XIV with thionyl chloride in the presence of a solvent such as pyridine to form a 3-aryl-1-chloro-2-fluoro-2-propene of formula XVIII, reacting the formula XVIII compound with triphenylphosphine to form an ylide of formula XIX, and reacting the formula XIX compound with a base such as sodium hydride and an aldehyde of formula XX.

FLOW DIAGRAM III

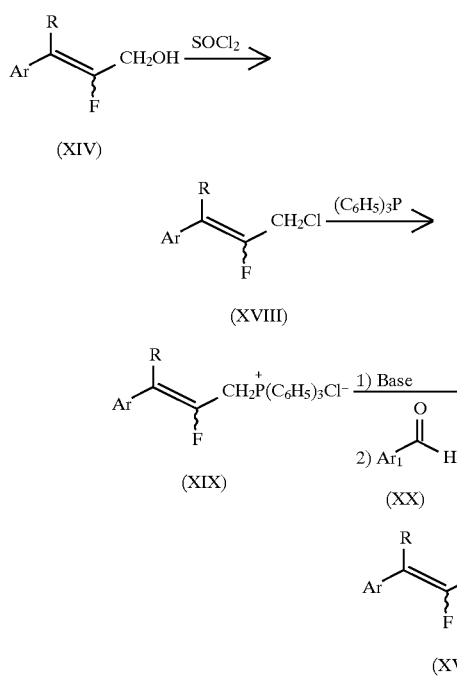

Advantageously, intermediate 3-aryl-2-fluoro-2-propenal compounds of formula XV may be prepared, as illustrated in Flow Diagram IV, by reacting an aldehyde or ketone of formula XI with an alkoxymethyl triphenyl phosphonium halide of formula XXI in the presence of a base such as butyllithium to form a 2-arylvinyl methyl ether of formula XXII, reacting the formula XXII compound with dichlorofluoromethane and a base such as potassium hydroxide in the presence of water and optionally a phase transfer catalyst such as 18-crown-6 to form an intermediate, and reacting the intermediate in situ with water at an elevated temperature, preferably about 60° to 90° C.

FLOW DIAGRAM IV

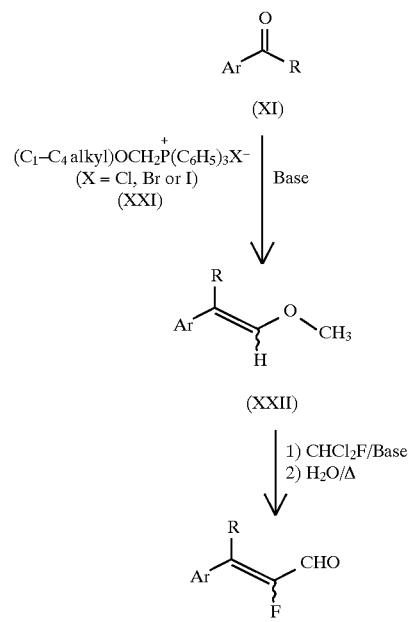

Formula I compounds wherein $R_2$ is Cl or Br may be prepared by halogenating a formula I compound wherein $R_2$ is hydrogen with a chlorinating agent such as N-chlorosuccinimide or a brominating agent such as N-bromosuccinimide. The reaction scheme is shown below in Flow Diagram V.

FLOW DIAGRAM V $$Ar-\underset{R_1}{\overset{R}{\underset{|}{\overset{|}{C}}}}-CF=CH-\underset{H}{\overset{R}{\underset{|}{\overset{|}{C}}}}-Ar_1 \xrightarrow{\text{halogenate}}$$

$$Ar-\underset{R_1}{\overset{R}{\underset{|}{\overset{|}{C}}}}-CF=CH-\underset{X}{\overset{H}{\underset{|}{\overset{|}{C}}}}-Ar_1$$

(X = Cl or Br)

Advantageously, formula I compounds wherein $R_2$ is cyano may be prepared by reacting a formula I compound wherein $R_2$ is Cl or Br with sodium cyanide. The reaction is shown in Flow Diagram VI.

FLOW DIAGRAM VI

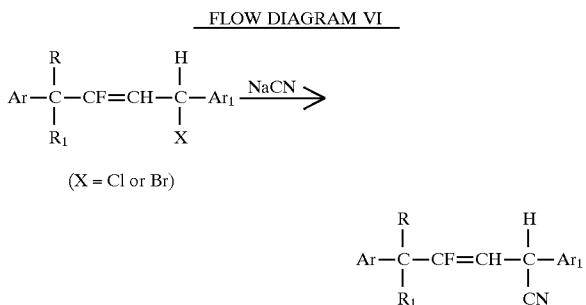

1,4-Diaryl-2-fluoro-2-butene compounds of formula I wherein $R_2$ is $OR_3$ may be prepared as shown below in Flow Diagram VII.

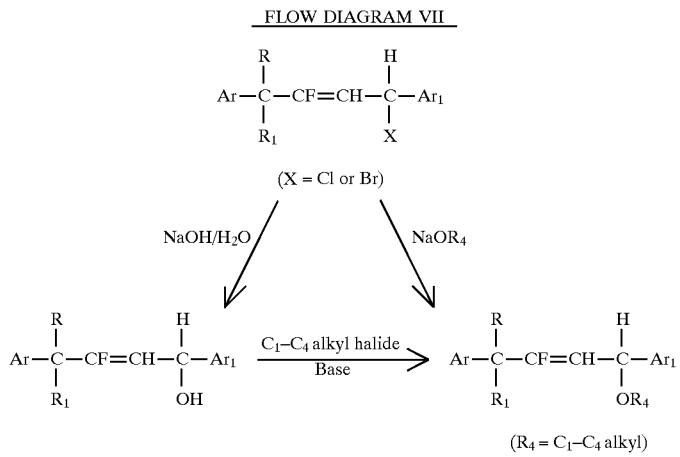

FLOW DIAGRAM VII

Formula I compounds wherein $R_2$ is Cl, Br or $OR_3$, and R and $R_1$ are other than hydrogen may be prepared as shown in Flow Diagram VIII.

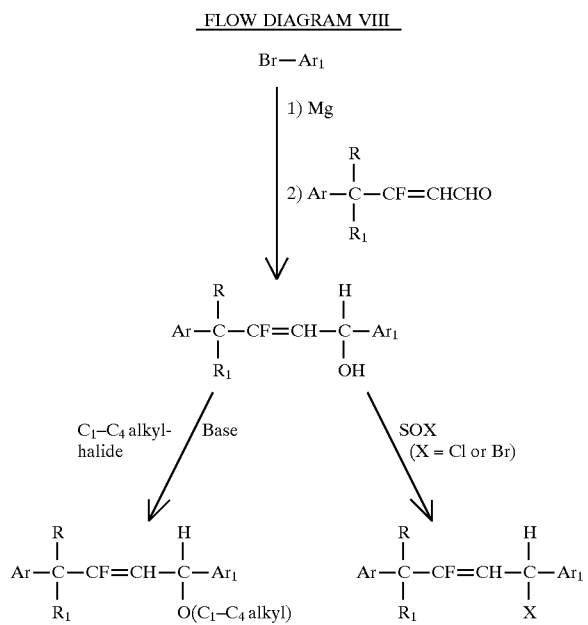

FLOW DIAGRAM VIII

The 1,4-diaryl-2-fluoro-2-butene compounds of the present invention are effective for controlling insect and acarid pests. Those compounds are also effective for protecting growing or harvested crops from damage caused by insect and acarid attack and infestation.

Insects controlled by the 1,4-diaryl-2-fluoro-2-butene compounds of this invention include Lepidoptera such as tobacco budworms, cabbage loopers, cotton boll worms, beet armyworms, southern armyworms and diamondback moths; Homoptera such as aphids, leaf hoppers, plant hoppers and white flies; Thysanoptera such as thrips; Coleoptera such as boll weevils, Colorado potato beetles, southern corn rootworms, western corn rootworms and mustard beetles; and Orthoptera such as locusts, crickets, grasshoppers and cockroaches. Acarina controlled by the compounds of this invention include mites such as two-spotted spider mites, carmine spider mites, banks grass mites, strawberry mites, citrus rust mites and leprosis mites.

In practice generally about 10 ppm to about 10,000 ppm and preferably about 100 ppm to about 5,000 ppm of a formula I compound, dispersed in water or another liquid carrier, is effective when applied to plants or the soil in which the plants are growing to protect the plants from insect and acarid attack and infestation.

The 1,4-diaryl-2-fluoro-2-butene compounds of this invention are also effective for controlling insect and acarid pests when applied to the foliage of plants and/or to the soil or water in which said plants are growing in sufficient amount to provide a rate of about 0.1 kg/ha to 4.0 kg/ha of active ingredient.

While the compounds of this invention are effective for controlling insect and acarid pests when employed alone, they may also be used in combination with other biological chemicals, including other insecticides and acaricides. For example, the formula I compounds of this invention may be used effectively in conjunction or combination with pyrethroids, phosphates, carbamates, cyclodienes, endotoxin of *Bacillus thuringiensis* (Bt), formamidines, phenol tin compounds, chlorinated hydrocarbons, benzoylphenyl ureas, pyrroles and the like.

The compounds of this invention may be formulated as emulsifiable concentrates, flowable concentrates or wettable powders which are diluted with water or other suitable polar solvent, generally in situ, and then applied as a dilute spray. Said compounds may also be formulated in dry compacted granules, granular formulations, dusts, dust concentrates, suspension concentrates, microemulsions and the like all of which lend themselves to seed, soil, water and/or foliage applications to provide the requisite plant protection. Such formulations or compositions of the present invention include a compound of the invention (or combinations thereof) admixed with one or more agronomically acceptable inert, solid or liquid carriers. Those compositions contain a pesticidally effective amount of said compound or compounds, which amount may vary depending upon the particular compound, target pest, and method of use. Those skilled in the art can readily determine what is a pesticidally effective amount without undue experimentation In order to facilitate a further understanding of the invention, the following examples are presented primarily for the purpose of illustrating more specific details thereof. The scope of the invention should not be deemed limited by

EXAMPLE 1

Preparation of p-Chloro-α-methylhydratroponitrile

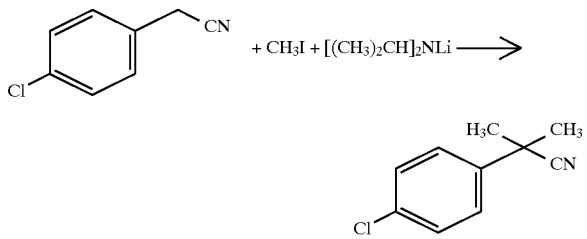

A solution of (p-chlorophenyl)acetonitrile (30.32 g, 0.20 mol) in tetrahydrofuran is treated dropwise with lithium diisopropylamide (0.44 mol, 220 mL of a 2M solution in heptane/tetrahydrofuran/benzene) at −25° C. to −30° C. over 60 minutes under nitrogen, stirred at −15° C. for one hour, treated dropwise with a solution of iodomethane (62.45 g, 0.44 mol) in tetrahydrofuran at −15° C., stirred at −15° C. for one hour, and diluted with water. The aqueous solution is extracted with ether The organic extract is washed sequentially with water, 2N hydrochloric acid and water, dried over anhydrous sodium sulfate, and concentrated in vacuo to obtain an oily residue. The residue is distilled to give the title product as a colorless oil (32.6 g, bp 89°–91° C./1 mm Hg, 90.7% yield).

EXAMPLE 2

Preparation of 2-(p-Chlorophenyl)-2-methylpropionaldehyde

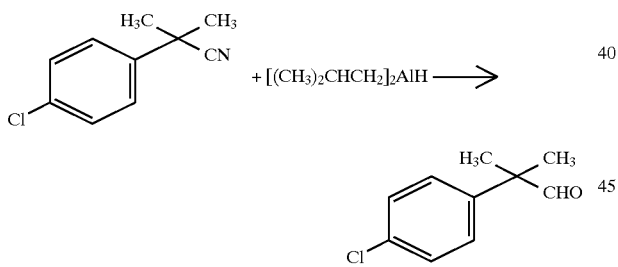

Diisobutylaluminum hydride (0.236 mol, 236 mL of a 1M solution in hexane) is added over 90 minutes to a solution of p-chloro-α-methylhydratroponitrile (32.6 g, 0.181 mol) in diethyl ether under nitrogen at 0° C. After the addition is complete, water and 6N hydrochloric acid are added to the reaction mixture while maintaining the temperature below 30° C. The resultant aqueous solution is stirred overnight at room temperature and extracted with diethyl ether. The organic extracts are combined, washed sequentially with 2N hydrochloric acid and water, dried over anhydrous sodium sulfate, and concentrated in vacuo to give the title product as an oil (31.1 g, 94% yield).

Using essentially the same procedure, but substituting 1-(p-chlorophenyl)cyclopropanecarbonitrile for p-chloro-α-methylhydratroponitrile, 1-(p-chlorophenyl) cyclopropanecarboxaldehyde is obtained as a colorless solid, mp 38°–41° C.

EXAMPLE 3

Preparation of 1.1-Dibromo-3-(p-chlorophenyl)-3-methyl-1-butene

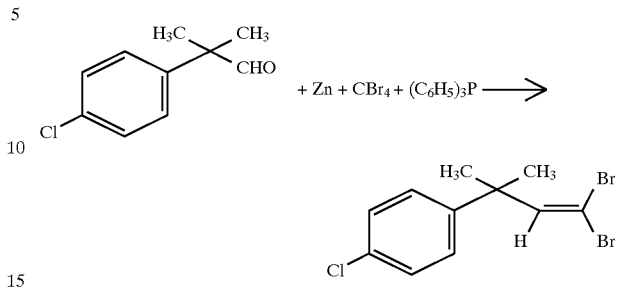

A solution of triphenyl phosphine (89.34 g, 0.34 mol) in methylene chloride is added dropwise to a mixture of zinc powder (22.27 g, 0.34 mol) and carbon tetrabromide (112.8 g, 0.34 mol) in methylene chloride at 20° C. over one hour. The resultant mixture is stirred at room temperature overnight, treated dropwise with a solution of 2-(p-chlorophenyl)-2-methylpropionaldehyde (31.1 g, 0.17 mol) in methylene chloride over 20 minutes, refluxed for 2 days, and poured into petroleum ether. The organic mixture is filtered through diatomaceous earth and concentrated in vacuo to obtain a residue. The residue is distilled to give the title product as an oil (38.5 g, bp 121°–123° C./0.3 mm Hg, 66.8% yield).

Using essentially the same procedure, but substituting 1-(p-chlorophenyl)cyclopropanecarboxaldehyde for 2-(p-chlorophenyl-2-methylpropionaldehyde, 1-(2,2-dibromovinyl)-1-(p-chlorophenyl)cyclopropane is obtained as a colorless oil.

EXAMPLE 4

Preparation of 4-(p-Chlorophenyl)-4-methyl-2-pentynenitrile

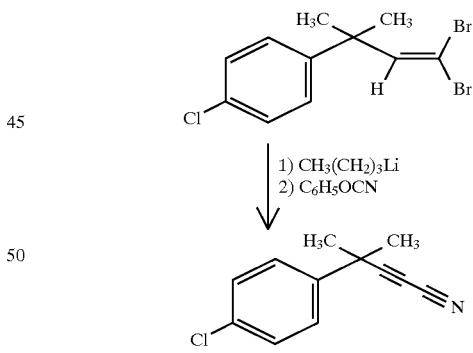

A solution of 1,1-dibromo-3-(p-chlorophenyl)-3-methyl-1-butene (38.5 g, 0.113 mol) in tetrahydrofuran is treated with n-butyllithium (0.25 mol, 100 mL of a 2.5M solution in hexane) under nitrogen over 45 minutes while maintaining the temperature below −65° C., stirred overnight at dry ice/acetone bath temperature, treated dropwise with a solution of phenyl cyanate (14.89 g, 0.125 mol) in tetrahydrofuran over 30 minutes at −65° C. to −70° C., allowed to warm to 10° C., and diluted with ethyl acetate and 5% sodium hydroxide solution. The resultant mixture is extracted with ethyl acetate. The organic extracts are combined, washed sequentially with 5% sodium hydroxide solution and water, dried over anhydrous sodium sulfate and concentrated in vacuo to obtain a residue. The residue is distilled to give the title product as an oil (18.7 g, bp 110°–113° C./0.9 mm Hg, 80.7% yield)

Using essentially the same procedure, but substituting 1-(2,2-dibromovinyl)- 1-(p-chlorophenyl)-cyclopropane for 1,1-dibromo-3-(p-chlorophenyl)-3-methyl-1-butene, 3-[1-(p-chlorophenyl)cyclopropyl]-2-propyne-1-carbonitrile is obtained as a yellow solid, mp 62°–64° C.

EXAMPLE 5

Preparation of 4-(p-Chlorophenyl)-3-fluoro-4-methyl-2-pentenenitrile, (Z)-

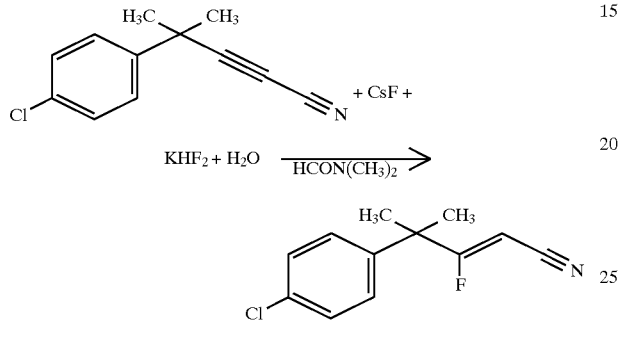

A mixture of cesium fluoride (41.38 g, 0.272 mol), potassium hydrogen fluoride (10.64 g, 0.136 mol) and water (13.07 g, 0.726 mol) in N,N-dimethylformamide is stirred for 10 minutes, treated with a solution of 4-(p-chlorophenyl)-4-methyl-2-pentynenitrile (18.5 g, 0.091 mol) in N,N-dimethylformamide, stirred at 80°–85° C. for 4 hours, stirred at room temperature overnight and diluted with water. The aqueous mixture is extracted with ethyl acetate. The organic extracts are combined, washed with water, dried over anhydrous sodium sulfate and concentrated in vacuo to obtain a residue. Column chromatography of the residue using silica gel and a 1:9 ethyl acetate/hexane solution gives the title product as an oil (15.6 g, 76.8% yield).

Using essentially the same procedure, but substituting 3-[1-(p-chlorophenyl)cyclopropyl]-2-propyne-1carbonitrile for 4-(p-chlorophenyl)-4-methyl-2-pentyne-nitrile, 1-(p-chlorophenyl)-β-fluorocyclopropaneacrylonitrile having a (Z)- to (E)- ratio of 9:1 is obtained as a colorless oil.

EXAMPLE 6

Preparation of 4-(p-Chlorophenyl)-4-methyl-2-pentenal, (Z)-

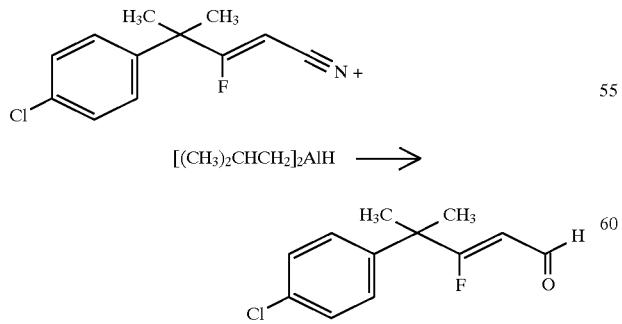

A solution of 4-(p-chlorophenyl)-3-fluoro-4-methyl-2-pentenenitrile, (Z)- (15.6 g, 69.7 mmol) in diethyl ether is treated dropwise with diisobutylaluminum hydride (83.6 mmol, 83.6 mL of a 1M solution in hexane) over 90 minutes at −45° C. under nitrogen, stirred at −40° C. for 35 minutes, and diluted sequentially with water and 2N hydrochloric acid at −10° C. The resultant aqueous mixture is stirred at room temperature for one hour and extracted with diethyl ether. The organic extracts are combined, washed.sequentially with water, 2N hydrochloric acid and water, dried over anhydrous sodium sulfate, and concentrated in vacuo to give the title product as a brown oil (15.34 g, 97% yield).

Using essentially the same procedure, but substituting 1-(p-chlorophenyl)-β-fluorocyclopropaneacrylonitrile having a (Z)- to (E)- ratio of 9:1 for 4-(p-chlorophenyl)-3-fluoro-4-methyl-2-pentenenitrile, (Z)-, 1-(p-chlorophenyl)-β-fluorocyclopropaneacrylaldehyde, (Z)- is obtained as a colorless oil.

EXAMPLE 7

Preparation of 4- (p-Chlorophenyl)-3-fluoro-4-methyl-2-penten-1-ol, (Z)-

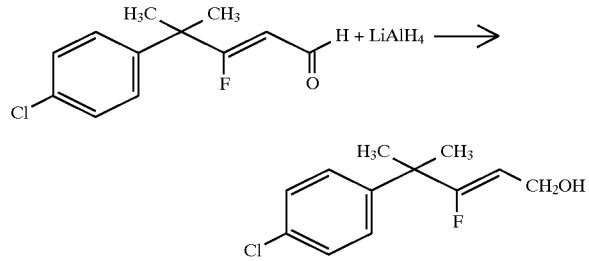

A solution of 4-(p-chlorophenyl)-4-methyl-2-pentenal, (Z)- (15.3 g: 67.5 mmol) in diethyl ether is added dropwise over 35 minutes to a mixture of lithium aluminum hydride (1.54 g, 40.5 mmol) in diethyl ether under nitrogen at −60° C. After the addition is complete, the reaction mixture is stirred for 20 minutes, and diluted sequentially with ethyl acetate, methanol and 2N hydrochloric acid. The resultant mixture is stirred for 20 minutes and extracted with ethyl acetate The combined organic extracts are washed sequentially with water and 2N hydrochloric acid, dried over anhydrous sodium sulfate, and concentrated in vacuo to obtain a residue. Flash chromatography of the residue using silica gel and a 2:8 ethyl acetate/hexane solution gives the title product as an oil (10.6 g, 68.7% yield).

Using essentially the same procedure, but substituting 1-(p-chlorophenyl)-β-fluorocyclopropaneacrylaldehyde, (Z)- for 4-(p-chlorophenyl)-4-methyl-2-pentenal, (Z)-, 1-(p-chlorophenyl)-β-fluorocyclopropaneallyl alcohol, (Z)- is obtained as a colorless oil.

EXAMPLE 8

Preparation of 1-Bromo-4-(p-chlorophenyl)-3-fluoro-4-methyl-2-pentene (Z)-

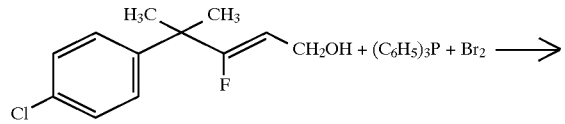

-continued

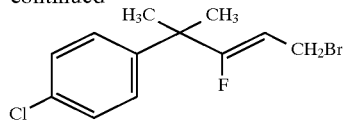

A solution of triphenyl phosphine (12.58 g, 55.6 mmol) in carbon tetrachloride at −5° C. to 5° C. is treated dropwise with a solution of bromine (8.89 g, 55.6 mmol) in carbon tetrachloride over 50 minutes under nitrogen, stirred at room temperature for one hour, treated with a solution of 4-(p-chlorophenyl)-3-fluoro-4-methyl-2-penten-1-ol, (Z)- (10.6 g, 46.3 mmol) in carbon tetrachloride over 15 minutes, refluxed for 2.5 hours, cooled to room temperature, and poured into petroleum ether. The resultant mixture is filtered through diatomaceous earth and concentrated in vacuo to obtain a residue. Flash chromatography of the residue using silica gel and a 1:9 ethyl acetate/hexane solution gives the title product as an oil (12.5 g, 92.6% yield).

Using essentially the same procedure, but substituting 1-(p-chlorophenyl)-β-fluorocyclopropaneallyl alcohol, (Z)- for 4-(p-chlorophenyl)-3-fluoro-4-methyl-2-penten-1-ol, (Z)-, 1-(p-chlorophenyl)-1-(3-bromo-1-fluoropropenyl) cyclopropane, (Z)- is obtained as a brown oil.

EXAMPLE 9

Preparation of 4-Fluoro-3-phenoxybenzeneboronic acid

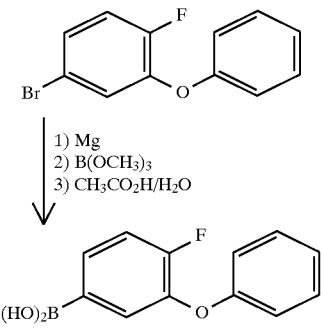

A solution of 5-bromo-2-fluorophenyl phenyl ether (8.01 g, 30 mmol) in tetrahydrofuran is added dropwise over 30 minutes to a mixture of magnesium turnings (0.0802 g, 33 mmol), a crystal of iodine and a few drops of 1,2-dibromoethane in tetrahydrofuran at 50°–55° C. under nitrogen. After the addition is complete, the reaction mixture is stirred at 50°–55° C. for 70 minutes and cooled to room temperature. The cooled mixture is added over 25 minutes to a solution of trimethyl borate (4.09 mL, 36 mmol) in diethyl ether at dry ice/acetone bath temperature. After the addition is complete, the mixture is stirred at dry ice/acetone bath temperature for 20 minutes, allowed to warm to −10° C. over 25 minutes, diluted sequentially with acetic acid and water, stirred at room temperature for 30 minutes, and extracted with ether. The organic extract is washed with water, dried over anhydrous sodium sulfate and concentrated in vacuo to obtain a residue. A mixture of the residue in water is heated over a steam bath for 30 minutes, cooled to room temperature and filtered to obtain a solid which is washed with hexanes and dried to give the title product as a colorless solid (5.7 g, mp 177°–180° C., 82% yield)

Using essentially the same procedure, the following compounds are obtained:

| X | Y |
|---|---|
| OC₆H₅ | H |
| H | OC₆H₅ |
| Cl | F |
| CH₃ | F |
| H | F |

EXAMPLE 10

Preparation of 4-(p-Chlorophenyl)-3-fluoro-1-(4-fluoro-3-phenoxyphenyl)-4-methyl-2-pentene (Z)-

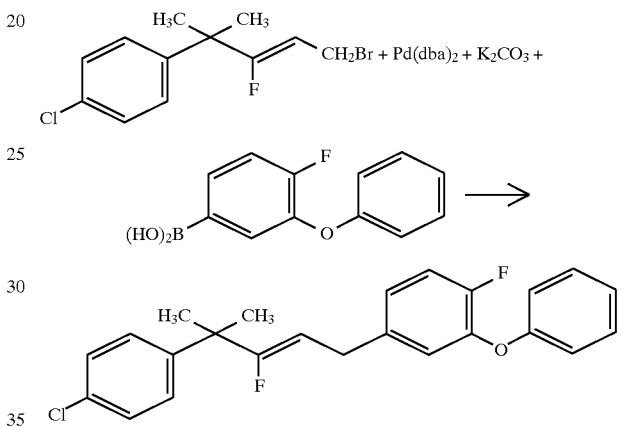

A mixture of 1-bromo-4-(p-chlorophenyl)-3-fluoro-4-methyl-2-pentene, (Z)- (1.02 g, 3.5 mmol), and bis(dibenzylideneacetone)palladium(0) (Pd(dba)₂, 0.1 g, 0.17 mmol) in toluene (20 mL) under nitrogen is stirred for one minute, treated with potassium carbonate (1.94 g, 0.014 mol), degassed, treated with a solution of 4-fluoro-3-phenoxybenzeneboronic acid (1.05 g, 4.55 mmol) in ethanol (5 mL), refluxed for 50 minutes, cooled to room temperature, diluted with ethyl acetate and filtered through diatomaceous earth. The filtrate is washed sequentially with water and brine, dried over anhydrous sodium sulfate and concentrated in vacuo to obtain a residue. Flash chromatography of the residue using silica gel and a 15:100 methylene chloride/hexane solution gives the title compound as a colorless oil (1.19 g, 85.6% yield) which is identified by NMR spectral analyses.

Using essentially the same procedure, the following compounds are obtained:

| R | R₁ | X | Y |
|---|----|---|---|
| CH₃ | CH₃ | OC₆H₅ | H¹ |
| —CH₂—CH₂— | | OC₆H₅ | H |

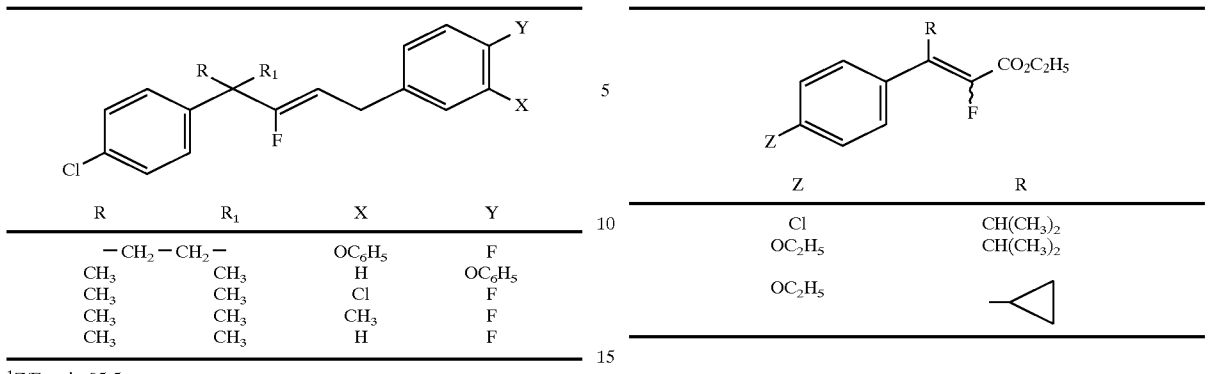

| R | R₁ | X | Y |
|---|---|---|---|
| —CH₂—CH₂— | | OC₆H₅ | F |
| CH₃ | CH₃ | H | OC₆H₅ |
| CH₃ | CH₃ | Cl | F |
| CH₃ | CH₃ | CH₃ | F |
| CH₃ | CH₃ | H | F |

¹Z/E ratio 95:5

EXAMPLE 11

Preparation of Ethyl p-chloro-β-cyclopropyl-α-fluorocinnamate, (E)- and (Z)-

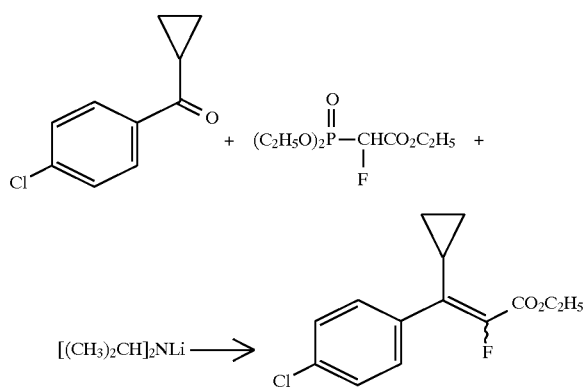

A solution of triethyl 2-fluoro-2-phosphonacetate (49 g, 0.202 mol) in ether is cooled to −55° to −60° C., treated dropwise over 17 minutes with a 2.0M solution of lithium diisopropylamide in heptane/tetrahydrofuran/ethylbenzene (116 mL, 0.232 mol), warmed to room temperature over 90 minutes, recooled to −55° to −60° C., treated over 10 minutes with a solution of 4-chlorophenyl cyclopropyl ketone (36.48 g, 0.202 mol) in ether, stirred at −55° to −60° C. for 20 minutes, warmed to and stirred at room temperature overnight, and quenched with water and 2 N hydrochloric acid (300 mL). The resultant aqueous mixture is extracted with ether. The organic extracts are combined, washed sequentially with water, 2N hydrochloric acid and water, dried over anhydrous sodium sulfate, and concentrated in vacuo to obtain a residue. Kugelrohr distillation of the residue gives the title product as an oil (50 g, 92%, b.p. 100°–110° C./0.5 mmHg).

Using essentially the same procedure, the following compounds are obtained:

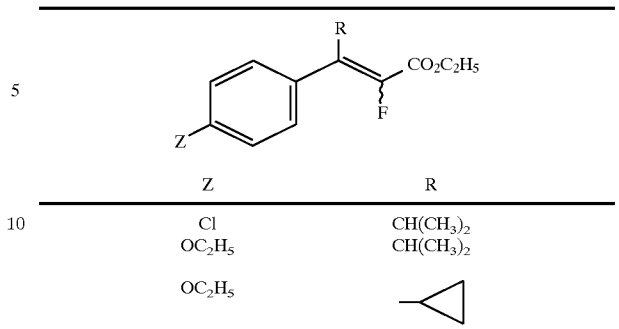

| Z | R |
|---|---|
| Cl | CH(CH₃)₂ |
| OC₂H₅ | CH(CH₃)₂ |
| OC₂H₅ | ◁ |

EXAMPLE 12

Preparation of 3-(p-Chlorophenyl)-3-cyclopropyl-2-fluoro-2-propen-1-ol, (E)- and (Z)-

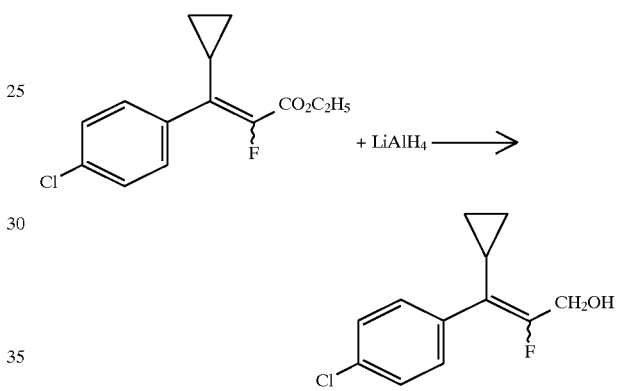

A solution of ethyl p-chloro-β-cyclopropyl-α-fluorocinnamate, (E)- and (Z)- (32.25 g, 0.12 mol) in ether is added dropwise to a mixture of lithium aluminum hydride (5.46 g, 0.144 mol) in ether while maintaining the temperature at −55° C. After the addition is complete, the reaction mixture is warmed to and stirred at −20° C. for 90 minutes, quenched sequentially with ethyl acetate, methanol and 2N hydrochloric acid, and extracted with ether. The organic extracts are combined, washed sequentially with water, saturated sodium hydrogen carbonate solution and water, dried over anhydrous sodium sulfate, and concentrated in vacuo to give the title product as a colorless oil (26.4 g, 97%).

Using essentially the same procedure, the following compounds are obtained:

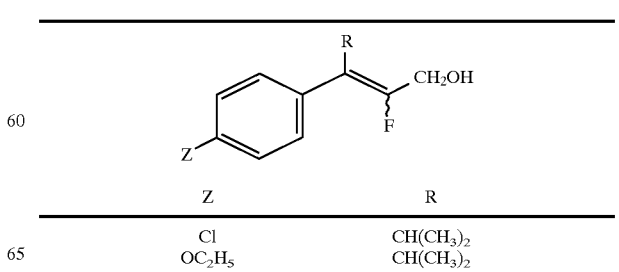

| Z | R |
|---|---|
| Cl | CH(CH₃)₂ |
| OC₂H₅ | CH(CH₃)₂ |

-continued

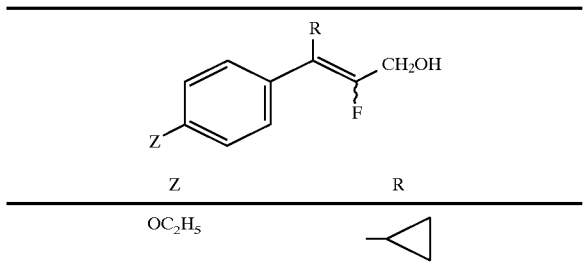

| Z | R |
|---|---|
| OC$_2$H$_5$ | △ |

EXAMPLE 13

Preparation of p-Chloro-β-cyclopropyl-α-fluorocinnamaldehyde

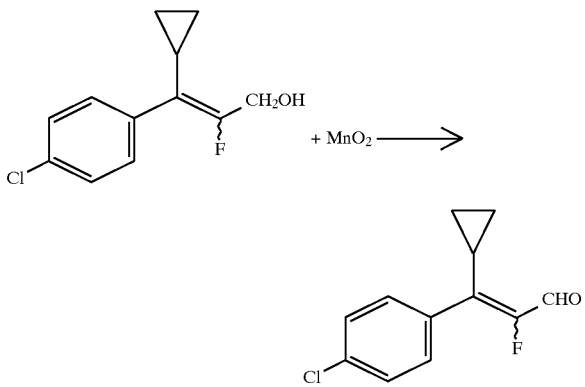

Activated manganese(IV) oxide (101.25 g, 1.16 mol) is added to a solution of 3-(p-chlorophenyl)-3-cyclopropyl-2-fluoro-2-propen-1-ol, (E)- and (Z)- (26.4 g, 0.116 mol) in hexanes. The resultant reaction mixture is stirred at room temperature overnight, filtered through a pad of diatomaceous earth, and concentrated in vacuo to obtain a residue. Flash column chromatography of the residue using silica gel and an ethyl acetate/hexanes solution (1:9) gives the title product as an oil (15.8 g, 60%).

Using essentially the same procedure, the following compounds are obtained:

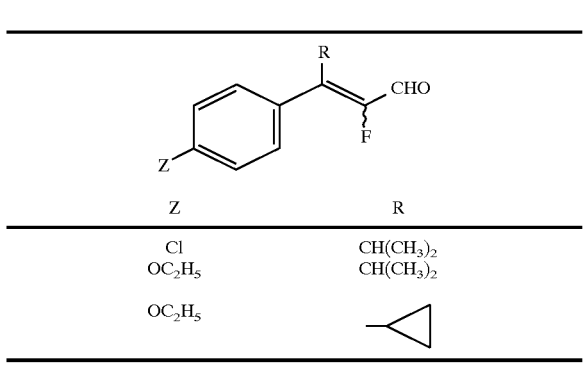

| Z | R |
|---|---|
| Cl | CH(CH$_3$)$_2$ |
| OC$_2$H$_5$ | CH(CH$_3$)$_2$ |
| OC$_2$H$_5$ | △ |

EXAMPLE 14

Preparation of 1-rl-(p-Chlorophenyl)-2-methoxyvinyll-cyclopropane. (E)- and (Z)-

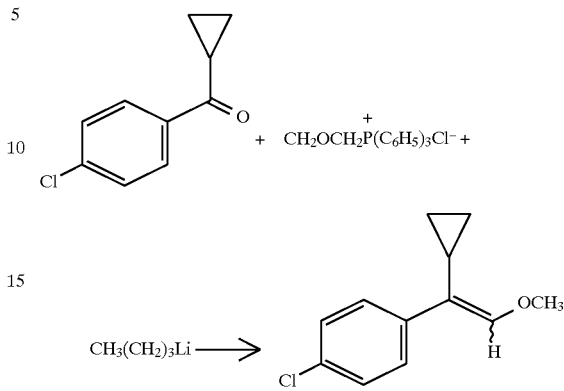

A solution of methoxymethyl triphenyl phosphonium chloride (20.5 g, 0.060 mol) in ether is cooled to −60° C., treated with a 2.5M solution of butyllithium in hexanes (25.2 mL, 0.063 mol), warmed to and stirred at 0°–5° C. for 90 minutes, recooled to −60° C., treated with a solution of 4-chlorophenyl cyclopropyl ketone (9.03 g, 0.050 mol) in ether, warmed to and stirred at room temperature overnight, quenched with ethyl acetate and 2N hydrochloric acid, and extracted with ethyl acetate. The organic extracts are combined, washed sequentially with water, 2N hydrochloric acid and water, dried over anhydrous sodium sulfate, and concentrated in vacuo to obtain a residue. Flash column chromatography of the residue using silica gel and an ethyl acetate/hexanes solution (1:9) gives the title product as an oil (6.2 g, 60%).

Using essentially the same procedure but substituting 4-fluorophenyl cyclopropyl ketone for 4-chlorophenyl cyclopropyl ketone, 1-[1-(p-fluorophenyl)-2-methoxyvinyl]-cyclopropane, (E)- and (Z)- is obtained as an oil.

EXAMPLE 15

Preparation of p-Chloro-β-cyclopropyl-α-fluorocinnamaldehyde

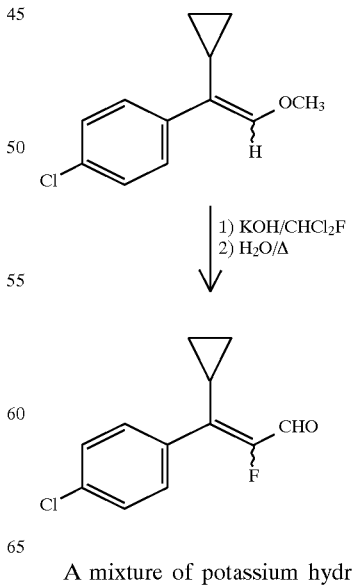

A mixture of potassium hydroxide (3.37 g, 0.060 mol), 18-Crown-6 (0.087 g, 0.33 mmol) and 1-[1-(p- chlorophenyl)-2-methoxyvinyl]cyclopropane, (E)- and (Z)- (3.13 g, 0.015 mol) in water is treated with dichlorofluoromethane (8 g, 0.077 mol) at 7°–10° C., stirred at 10°–13° C. overnight, treated with additional dichlorofluoromethane (6 g, 0.058 mol) at 7°–10° C., stirred at 10°–13° C. for 36 hours, treated with water, stirred at 70°–75° C. for 4 hours, cooled to room temperature, and extracted with ethyl acetate. The organic extracts are combined, washed sequentially with water, 2N hydrochloric acid and water, dried over anhydrous sodium sulfate, and concentrated in vacuo to obtain a residue. Flash column chromatography of the residue using silica gel and an ethyl acetate/hexanes solution (1:9) gives 1.02 g of the E-isomer of the title product and 0.69 g of the Z-isomer of the title product (1.71 g total product).

Using essentially the same procedure, but substituting 1-[1-(p-fluorophenyl)-2-methoxyvinyl]cyclopropane, (E)- and (Z)- for 1-[1-(p-chlorophenyl)-2-methoxyvinyl]cyclopropane, (E)- and (Z)-, β-cyclopropyl-p,α-difluorocinnamaldehyde is obtained as an oil.

EXAMPLE 16

Preparation of (4-Fluoro-3-phenoxybenzyl)triphenyl phosphonium bromide

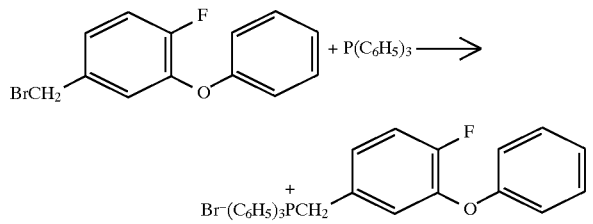

A solution of 4-fluoro-3-phenoxybenzyl bromide (42.17 g, 0.150 mol) in toluene is added to a solution of triphenyl phosphine (41.31 g, 0.158 mol) in toluene. The resultant reaction mixture is refluxed for one hour, cooled to room temperature, and filtered to obtain a solid. The solid is washed sequentially with toluene and hexanes, and dried in a dessicator at 60° C. to give the title product (73.7 g, 90.4%) which is identified by NMR spectral analyses.

Using essentially the same procedure, the following compounds are obtained:

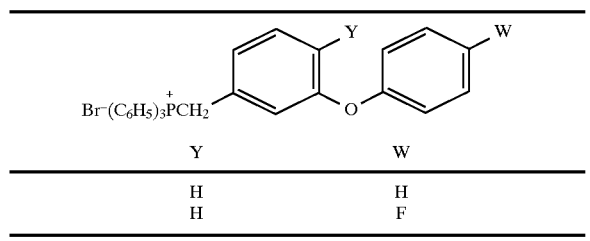

| Y | W |
|---|---|
| H | H |
| H | F |

EXAMPLE 17

Preparation of 1-(p-Chlorophenyl)-1-cyclopropyl-2-fluoro-4-(4-fluoro-3-phenoxyphenyl)-1,3-butadiene

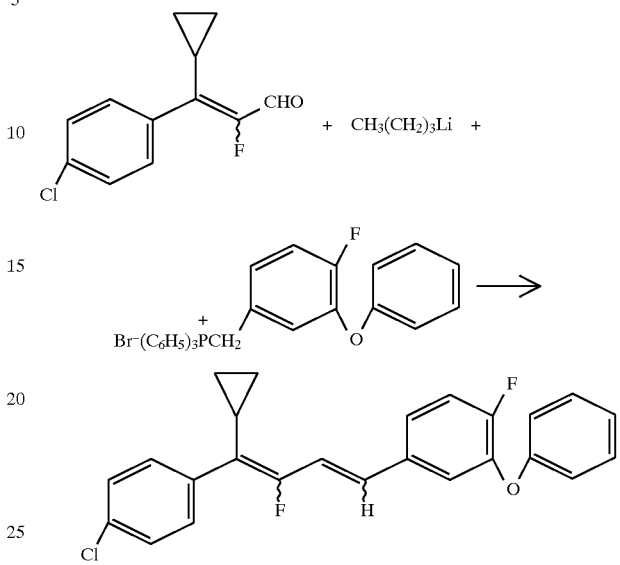

A mixture of (4-fluoro-3-phenoxybenzyl)triphenyl phosphonium bromide (41.77 g, 0.077 mol) in tetrahydrofuran is cooled to −55° to −60° C., treated dropwise with a 2.5M solution of butyllithium in hexanes (32.15 mL, 0.080 mol), warmed to and stirred at room temperature for 2 hours, cooled to −55° to −60° C., treated dropwise with a solution of 2-fluoro-3-cyclopropyl-3-(p-chlorophenyl)acrylaldehyde (15.7 g, 0.070 mol) in tetrahydrofuran, warmed to and stirred at room temperature overnight, and quenched with ethyl acetate and 2N hydrochloric acid. The resultant aqueous mixture is extracted with ethyl acetate. The organic extracts are combined, washed sequentially with water, 2N hydrochloric acid and water, dried over anhydrous sodium sulfate, and concentrated in vacuo to obtain a residue. Flash column chromatography of the residue using silica gel and an ethyl acetate/hexanes solution (1:9) gives the title product as an oil (26.0 g, 91%).

Using essentially the same procedure, the following compounds are obtained:

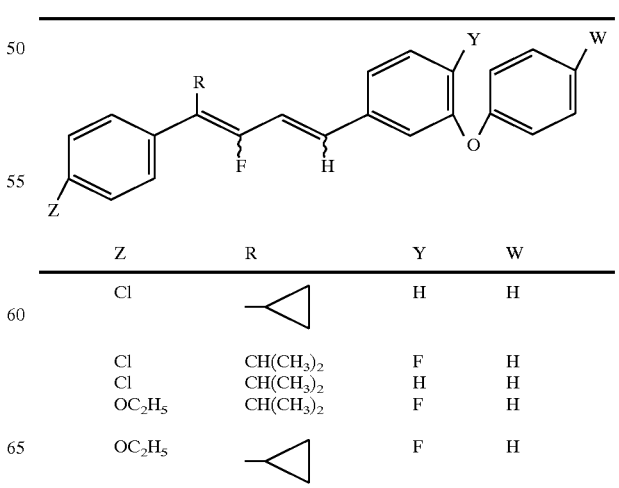

| Z | R | Y | W |
|---|---|---|---|
| Cl | ◁ | H | H |
| Cl | CH(CH$_3$)$_2$ | F | H |
| Cl | CH(CH$_3$)$_2$ | H | H |
| OC$_2$H$_5$ | CH(CH$_3$)$_2$ | F | H |
| OC$_2$H$_5$ | ◁ | F | H |

-continued

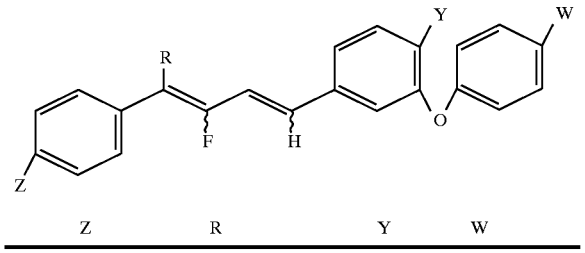

| Z | R | Y | W |
|---|---|---|---|
| OC$_2$H$_5$ | CH(CH$_3$)$_2$ | H | H |
| OC$_2$H$_5$ | CH(CH$_3$)$_2$ | H | F |
| Cl | cyclopropyl | H | F |
| F | cyclopropyl | F | H |
| OC$_2$H$_5$ | cyclopropyl | H | H |
| F | cyclopropyl | H | H |

| Z | R | Y | W |
|---|---|---|---|
| Cl | cyclopropyl | H | H |
| Cl | CH(CH$_3$)$_2$ | F | H |
| Cl | CH(CH$_3$)$_2$ | H | H |
| OC$_2$H$_5$ | CH(CH$_3$)$_2$ | F | H |
| OC$_2$H$_5$ | cyclopropyl | F | H |
| OC$_2$H$_5$ | CH(CH$_3$)$_2$ | H | H |
| OC$_2$H$_5$ | CH(CH$_3$)$_2$ | H | F |
| Cl | cyclopropyl | H | F |
| F | cyclopropyl | F | H |
| OC$_2$H$_5$ | cyclopropyl | H | H |
| F | cyclopropyl | H | H |

EXAMPLE 18

Preparation of 1-[1-(p-Chlorophenyl)-2-fluoro-4-(4-fluoro-3-phenoxyphenyl)-2-butenyl]cyclopropane. (R,S)-(Z)-

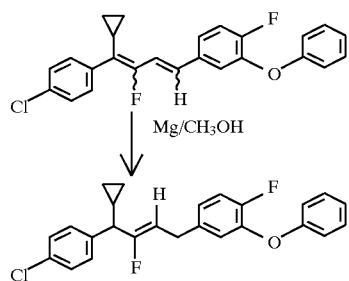

A solution of 1-(p-chlorophenyl)-1-cyclopropyl-2-fluoro-4-(4-fluoro-3-phenoxyphenyl)-1,3-butadiene (26 g, 0.064 mol) in a methanol/tetrahydrofuran solution (15:1) is treated with magnesium turnings (7.72 g, 0.317 mol), stirred at room temperature for 4 hours, quenched with hydrochloric acid, and extracted with ethyl acetate. The organic extracts are combined, washed sequentially with water, 2N hydrochloric acid and water, dried over anhydrous sodium sulfate, and concentrated in vacuo to obtain a residue. Flash column chromatography of the residue using silica gel and an ethyl acetate/hexanes solution (5:95) gives the title product as an oil (21.4 g, 82%) which is identified by NMR spectral analyses.

Using essentially the same procedure, the following compounds are obtained:

EXAMPLE 19

Insecticidal and acaricidal evaluation of test compounds

Test solutions are prepared by dissolving the test compound in a 35% acetone in water mixture to give a concentration of 10,000 ppm. Subsequent dilutions are made with water as needed.

*Spodoptera eridania*, 3rd instar larvae, southern armyworm (SAW)

A Sieva lima bean leaf expanded to 7–8 cm in length is dipped in the test solution with agitation for 3 seconds and allowed to dry in a hood. The leaf is then placed in a 100×10 mm petri dish containing a damp filter paper on the bottom and ten 3rd instar caterpillars. At 5 days, observations are made of mortality, reduced feeding, or any interference with normal molting.

*Diabrotica virgifera virgifera* Leconte, 3rd instar western corn rootworm (WCR)

One cc of fine talc is placed in a 30 mL wide-mouth screw-top glass jar. One mL of the appropriate acetone test solution is pipetted onto the talc so as to provide 1.25 mg of active ingredient per jar. The jars are set under a gentle air flow until the acetone is evaporated. The dried talc is loosened, 1 cc of millet seed is added to serve as food for the insects and 25 mL of moist soil is added to each jar The jar is capped and the contents thoroughly mixed mechanically. Following this, ten 3rd instar rootworms are added to each jar and the jars are loosely capped to allow air exchange for the larvae. The treatments are held for 5 days when mortality counts are made. Missing larvae are presumed dead, since they decompose rapidly and cannot be found. The concentrations of active ingredient used in this test correspond approximately to 50 kg/ha.

*Heliothis virenscens*, 3rd instar tobacco budworm (TBW)

Cotton cotyledons are dipped in the test solution and allowed to dry in a hood. When dry, each is cut into quarters and ten sections are placed individually in 30 mL plastic medicine cups containing a 5 to 7 mm long piece of damp dental wick. One 3rd instar caterpillar is added to each cup and a cardboard lid placed on the cup. Treatments are maintained for 3 days before mortality counts and estimates of reduction in feeding damage are made.

*Aphis fabae*, mixed instar, bean aphid (BA)

Pots containing single nasturtium plants (Tropaeolum sp.) about 5 cm tall are infested with about 100–200 aphids one day before the test. Each pot is sprayed with the test solution for 2 revolutions of a 4 rpm turntable in a hood. The spray is directed to give complete coverage of the plants and aphids, The sprayed pots are set on their sides on white trays and held for 2 days, following which mortality estimates are made.

*Tetranychus urticae* (OP-resistant strain), 2-spotted spider mite (TSM)

Sieva lima bean plants with primary leaves expanded to 7–8 cm are selected and cut back to one plant per pot. A small piece is cut from an infested leaf taken from the main colony and placed on each leaf of the test plants. This is done about 2 hours before treatment to allow the mites to move over to the test plant to lay eggs. The size of the cut, infested leaf is varied to obtain about 100 mites per leaf. At the time of test treatment, the piece of leaf used to transfer the mites is removed and discarded. The newly-infested plants are dipped in the test solution for 3 seconds with agitation and set in the hood to dry. After 2 days, one leaf is removed and mortality counts are made.

The tests are rated according to the scale shown below and the data obtained are shown in Table I.

Compounds employed in the above-described evaluations are given a compound number and identified by name. Data in Table I are reported by compound number.

| | |
|---|---|
| 0 = no effect | 5 = 56–65% kill |
| 1 = 10–25% kill | 6 = 66–75% kill |
| 2 = 26–35% kill | 7 = 76–85% kill |
| 3 = 36–45% kill | 8 = 86–99% kill |
| 4 = 46–55% kill | 9 = 100% kill |

— = not tested

COMPOUNDS EVALUATED AS INSECTICIDAL AND ACARICIDAL AGENTS

| Compound Number | |
|---|---|
| 1 | 4-(p-Chlorophenyl)-3-fluoro-4-methyl-1-(m-phenoxyphenyl)-2-pentene, (Z)- and (E)- (95:5) |
| 2 | 4-(p-Chlorophenyl)-3-fluoro-1-(4-fluoro-3-phenoxyphenyl)-4-methyl-2-pentene, (Z)- |
| 3 | 1-(p-Chlorophenyl)-1-[1-fluoro-3-(m-phenoxyphenyl)propenyl] cyclopropane, (Z)- |
| 4 | 1-(p-Chlorophenyl)-1-[1-fluoro-3-(4-fluoro-3-phenoxyphenyl)propenyl]cyclopropane, (Z)- |
| 5 | 4-(p-Chlorophenyl)-3-fluoro-4-methyl-1-(p-phenoxyphenyl)-2-pentene, (Z)- |
| 6 | 1-(3-Chloro-4-fluorophenyl)-4-(p-chlorophenyl)-3-fluoro-4-methyl-2-pentene, (Z)- |
| 7 | 4-(p-Chlorophenyl)-3-fluoro-1-(4-fluoro-m-tolyl)-4-methyl-2-pentene, (Z)- |
| 8 | 1-[1-(p-Chlorophenyl)-2-fluoro-4-(4-fluoro-3-phenoxyphenyl)-butenyl]cyclopropane, (R,S)- (Z)- |
| 9 | 1-[1-(p-Chlorophenyl)-2-fluoro-4-(m-phenoxy- |

-continued

| Compound Number | |
|---|---|
| | phenyl)-2-butenyl]cyclopropane, (R,S)- (Z)- |
| 10 | 4-(p-Chlorophenyl)-3-fluoro-1-(4-fluoro-3-phenoxyphenyl)-5-methyl-2-hexene, (R,S)-(Z)- |
| 11 | 4-(p-Chlorophenyl)-3-fluoro-5-methyl-1-(m-phenoxyphenyl)-2-hexene, (R,S)- (Z)- |
| 12 | 4-(p-Ethoxyphenyl)-3-fluoro-1-(4-fluoro-3-phenoxyphenyl)-5-methyl-2-hexene, (R,S)-(Z)- |
| 13 | 1-[1-(p-Ethoxyphenyl)-2-fluoro-4-(4-fluoro-3-phenoxyphenyl)-2-butenyl]cyclopropane, (R,S)- (Z)- |
| 14 | 4-(p-Ethoxyphenyl)-3-fluoro-5-methyl-1-(m-phenoxyphenyl)-2-hexene, (R,S)- (Z)- |
| 15 | 4-(p-Ethoxyphenyl)-3-fluoro-1-[m-(p-fluorophenoxy)phenyl]-5-methyl-2-hexene, (R,S)- (Z)- |
| 16 | 1-{1-(p-Chlorophenyl)-2-fluoro-4-[m-(p-fluorophenoxy)phenyl]-2-butenyl}cyclopropane, (R,S)-(Z)- |
| 17 | 1-[2-Fluoro-4-(4-fluoro-3-phenoxyphenyl)-1-(p-fluorophenyl)-2-butenyl]cyclopropane, (R,S)- (Z)- |
| 18 | 1-[1-(p-Ethoxyphenyl)-2-fluoro-4-(m-phenoxyphenyl)-2-butenyl]cyclopropane, (R,S)- (Z)- |
| 19 | 1-[2-Fluoro-1-(p-fluorophenyl)-4-(m-phenoxyphenyl)-2-butenyl]cyclopropane, (R,S)- (Z)- |

TABLE I

Insecticidal And Acaricidal Evaluations

| Compound Number | SAW (100 ppm) | WCR (50 ppm) | TBW (100 ppm) | BA (100 ppm) | TSM (300 ppm) | (100 ppm) |
|---|---|---|---|---|---|---|
| 1 | 9 | 9 | 9 | 5 | 8 | 0 |
| 2 | 9 | 9 | 9 | 9 | 0 | — |
| 3 | 9 | 9 | 9 | 9 | 0 | — |
| 4 | 9 | 9 | 9 | 9 | 2 | — |
| 5 | 0 | 0 | 0 | 4 | 1 | 3 |
| 6 | 0 | 0 | 1 | 0 | 1 | 2 |
| 7 | 0 | 6 | 0 | 4 | — | 0 |
| 8 | 9 | 9 | 9 | 9 | — | 7 |
| 9 | 9 | 9 | 9 | 8 | — | 8 |
| 10 | 9 | 9 | 9 | 8 | 8 | 0 |
| 11 | 9 | 9 | 9 | 7 | 8 | 0 |
| 12 | 9 | 9 | 9 | 9 | — | 0 |
| 13 | 9 | 9 | 9 | 9 | — | 9 |
| 14 | 9 | 9 | 9 | 8 | — | 0 |
| 15 | 9 | 9 | 9 | 3 | — | 0 |
| 16 | 9 | 9 | 9 | 8 | — | 7 |
| 17 | 9 | 9 | 9 | 9 | — | 7 |
| 18 | 9 | 9 | 9 | 9 | — | 8 |
| 19 | 9 | 9 | 9 | 9 | — | 2 |

We claim:

1. A compound having the structural formula

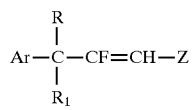

wherein

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, or $C_1$–$C_4$alkyl, $C_1$–$C_4$haloalkyl, $C_1$–$C_4$alkoxy or $C_1$–$C_4$haloalkoxy groups, R and $R_1$ are each independently $C_1$–$C_4$alkyl, $C_1$–$C_4$haloalkyl, $C_3$–$C_6$cycloalkyl or $C_3$–$C_6$halocycloalkyl, or R and $R_1$ taken together with the carbon atom to which they are attached form a $C_3$–$C_6$cycloalkyl ring optionally substituted with any combination of from one to three halogen or $C_1$–$C_4$alkyl groups; and Z is cyano, CHO, $CH_2OH$ or $CH_2Br$, and the optical isomers thereof, and the cis and trans isomers thereof.

2. The compound according to claim 1 wherein

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups.

3. The compound according to claim 2 wherein

R and $R_1$ are methyl, or R and $R_1$ taken together with the carbon atom to which they are attached form a cyclopropyl ring.

4. The compound according to claim 1 wherein Z is cyano, CHO or $CH_2OH$.

5. The compound according to claim 1 wherein R and $R_1$ are each independently $C_1$–$C_4$alkyl, $C_1$–$C_4$naloalkyl, $C_3$–$C_6$cycloalkyl, or $C_3$–$C_6$halocycloalkyl.

6. The compound according to claim 5 wherein Ar is phenyl optionally substituted with any combination of from one to three halogen, $C_1$–$C_4$alkyl, $C_1$–$C_4$haloalkyl, $C_1$–$C_4$alkoxy, or $C_1$–$C_4$haloalkoxy groups.

* * * * *